(12) United States Patent
Adler et al.

(10) Patent No.: US 8,541,853 B1
(45) Date of Patent: Sep. 24, 2013

(54) HIGH FREQUENCY CMUT

(75) Inventors: Steven Adler, Saratoga, CA (US); Peter Johnson, Sunnyvale, CA (US); Ira Oaktree Wygant, Palo Alto, CA (US)

(73) Assignee: Texas Instruments Incorporated, Dallas, TX (US)

( * ) Notice: Subject to any disclaimer, the term of this patent is extended or adjusted under 35 U.S.C. 154(b) by 42 days.

(21) Appl. No.: 13/427,856

(22) Filed: Mar. 22, 2012

(51) Int. Cl.
*H01L 29/84* (2006.01)

(52) U.S. Cl.
USPC ............ 257/416; 257/415; 257/E29.324; 257/E21.002; 257/E29.111; 438/53

(58) Field of Classification Search
USPC ............ 257/415–416, E29.324, E21.002, 257/E29.111; 438/53
See application file for complete search history.

(56) References Cited

U.S. PATENT DOCUMENTS

| | | |
|---|---|---|
| 6,430,109 B1 | 8/2002 | Khuri-Yakub et al. |
| 7,074,634 B2 | 7/2006 | Foglietti et al. |
| 7,489,593 B2 | 2/2009 | Nguyen-Dinh et al. |
| 2004/0085858 A1 | 5/2004 | Khuri-Yakub et al. |
| 2006/0075818 A1 | 4/2006 | Huang et al. |
| 2009/0029501 A1* | 1/2009 | Weigold .................. 438/53 |

* cited by examiner

*Primary Examiner* — Jami M Valentine
(74) *Attorney, Agent, or Firm* — Eugene C. Conser; W. James Brady; Frederick J. Telecky, Jr.

(57) ABSTRACT

A high-frequency capacitive micromachined ultrasonic transducer (CMUT) has a silicon membrane and an overlying metal silicide layer that together form a conductive structure which can vibrate over a cavity. The CMUT also has a metal structure that touches a group of conductive structures. The metal structure has an opening that extends completely through the metal structure to expose the conductive structure.

18 Claims, 19 Drawing Sheets

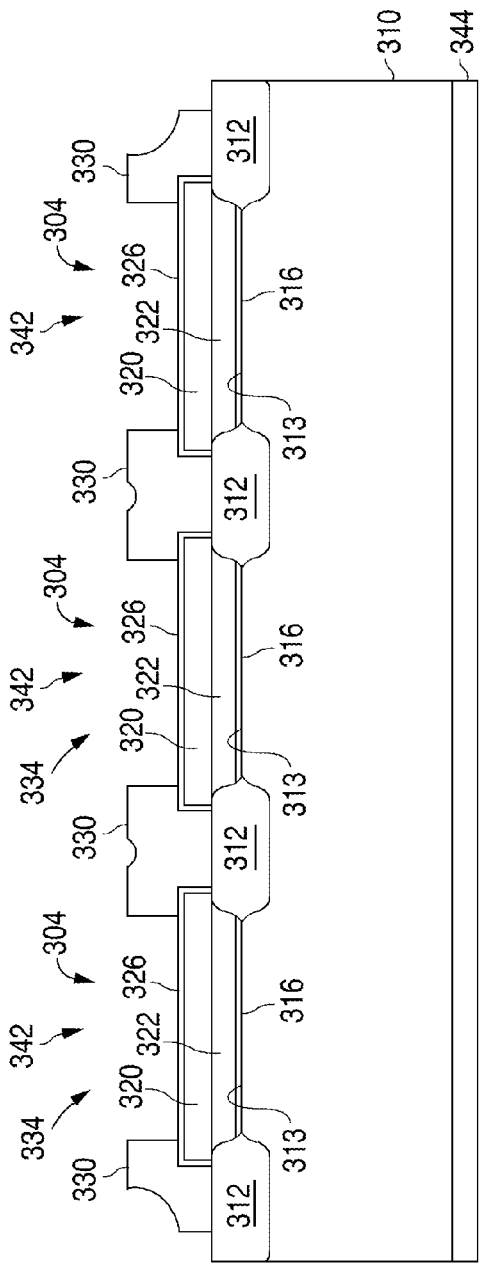
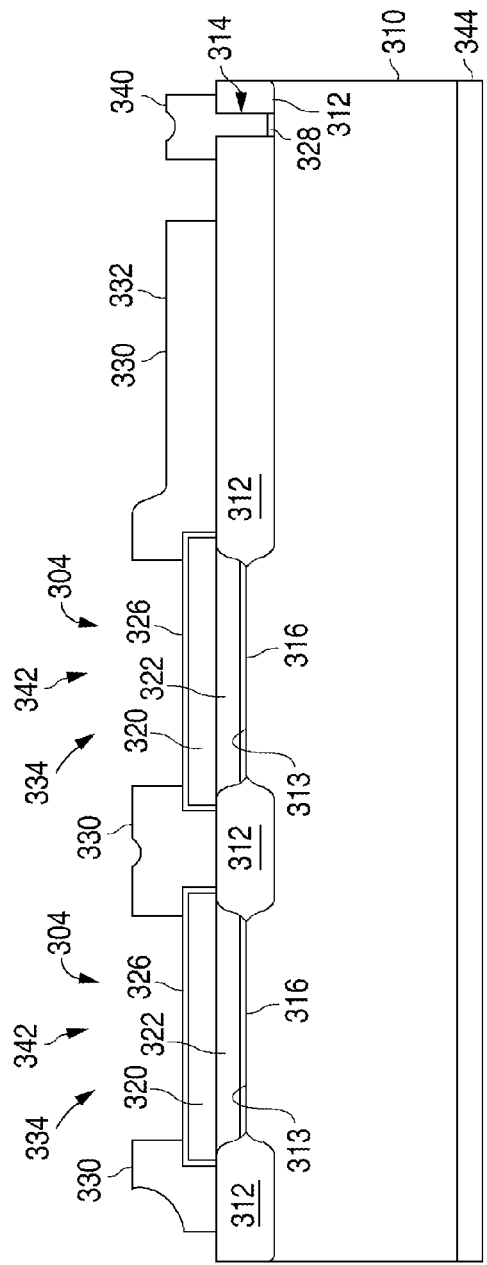
FIG. 3B
FIG. 3C

HIGH FREQUENCY CMUT

BACKGROUND OF THE INVENTION

1. Field of the Invention

The present invention relates to a CMUT and, more particularly, to a high frequency CMUT.

2. Description of the Related Art

A capacitive micromachined ultrasonic transducer (CMUT) is a semiconductor-based ultrasonic transducer that utilizes a change in capacitance to convert received ultrasonic waves into an electrical signal, and to convert an alternating electrical signal into transmitted ultrasonic waves.

FIGS. 1A-1C show views that illustrate a prior-art CMUT array 100. FIG. 1A shows a plan view of CMUT array 100, while FIG. 1B shows a cross-sectional view of CMUT array 100 taken along line 1B-1B of FIG. 1A, and FIG. 1C shows a cross-sectional view of CMUT array 100 taken along line 1C-1C of FIG. 1A.

As shown in FIGS. 1A-1C, CMUT array 100 has three CMUT elements 102 arranged in a single row, where each CMUT element 102 has 12 CMUT cells 104 arranged in an array three CMUT cells wide by four CMUT cells long. Further, each adjacent pair of CMUT elements 102 has a minimum spacing X of 16 µm, while each adjacent pair of CMUT cells 104 have a minimum spacing Y of 5 µm.

CMUT array 100 also has a conventionally-formed semiconductor substrate 110, and a post oxide structure 112 that touches semiconductor substrate 110. Semiconductor substrate 110 has a top surface which, in turn, has a number of spaced-apart CMUT surface regions 113. Further, semiconductor substrate 110 is heavily doped to have a resistance of 0.01 Ω/cm or less. Post oxide structure 112 horizontally surrounds, but does not cover, each CMUT surface region 113. In addition, post oxide structure 112 has substrate contact openings 114 that extend completely through post oxide structure 112 to expose semiconductor substrate 110.

As additionally shown in FIGS. 1A-1C, CMUT array 100 includes a number of cell oxide structures 116, a corresponding number of silicon membranes 120, and a corresponding number of vacuum-sealed cavities 122. The cell oxide structures 116 touch the CMUT surface regions 113 on the top surface of semiconductor substrate 110. The silicon membranes 120 touch the top surface of post oxide structure 112 and lie over and spaced apart from the cell oxide structures 116. The vacuum-sealed cavities 122, which are horizontally surrounded by post oxide structure 112, lie vertically between the cell oxide structures 116 and the silicon membranes 120. Each of the silicon membranes 120 is approximately 2.2 µm thick.

CMUT array 100 also includes a number of aluminum plates 126 (which can optionally include copper). Each aluminum plate 126 touches and covers the top surfaces of a group of silicon membranes 120, where an aluminum plate 126 and a group of silicon membranes 120 are part of a CMUT element 102. The aluminum plates 126 reduce the sheet resistances of the silicon membranes 120, and provide low-resistance paths to bond pad regions 128 on the top surfaces of the aluminum plates 126. For example, a 1500 Å-thick aluminum plate has a sheet resistance of approximately 180 mΩ/square.

Further, CMUT array 100 includes a number of aluminum bond pads 130 (which can optionally include copper) that lie within the substrate contact openings 114 to touch semiconductor substrate 110. In addition, CMUT array 100 includes a passivation layer 132 approximately 2000 Å thick that touches and lies over post oxide structure 112, the aluminum plates 126, and the aluminum bond pads 130. Passivation layer 132, in turn, has a number of bond pad openings 136 that expose the aluminum bond pads 130, and a number of bond pad openings 138 that expose the bond pad regions 128 on the top surfaces of the aluminum plates 126.

The silicon membranes 120, the overlying portions of the aluminum plates 126, and the overlying portions of passivation layer 132 form a number of membrane stacks 140 that lie directly over a corresponding number of vacuum-sealed cavities 122. The membrane stacks 140, along with the vacuum-sealed cavities 122 and the cell oxide structures 116, form the CMUT cells 104. Further, CMUT array 100 has an acoustic dampening structure 142 that touches the bottom surface of semiconductor substrate 110.

In operation, a first bias voltage is placed on semiconductor substrate 110, which functions as a first capacitor plate, and a second bias voltage is placed on the silicon membranes 120, which function as second capacitor plates. Thus, the voltages across the capacitor plates lie across the vacuum-sealed cavities 122. When used as a receiver, an ultrasonic wave causes the membrane stacks 140 to vibrate. The vibration varies the capacitance across the first and second capacitor plates, thereby generating an electrical signal that varies as the capacitance varies.

When used as a transmitter, an alternating electrical signal applied across the biased first and second capacitor plates causes the membrane stacks 140 to vibrate which, in turn, transmits ultrasonic waves. The rate or frequency at which a membrane stack 140 vibrates depends on a number of factors, including the lateral dimensions of vacuum-sealed cavity 122, and the stiffness of membrane stack 140. The stiffness of membrane stack 140, in turn, depends in part on the thickness of membrane stack 140.

In addition to transmitting ultrasonic waves outward, ultrasonic waves are also transmitted backward towards the bottom surface of semiconductor substrate 110. These backward ultrasonic waves can resonate within semiconductor substrate 110 depending on the thickness of semiconductor substrate 110 and the frequency of operation, and can interfere with the quality of the resultant image. Acoustic dampening structure 142 absorbs and dampens the ultrasonic waves in semiconductor substrate 110.

FIGS. 2A-2N show cross-sectional views that illustrate a prior-art method 200 of forming a CMUT structure. As shown in FIG. 2A, method 200 utilizes a conventionally-formed single-crystal silicon wafer 210. Silicon wafer 210 has rows and columns of die-sized regions, and one or more CMUT cells can be simultaneously formed in each die-sized region.

For simplicity, rather than showing the simultaneous formation of two or more identical CMUT cells, FIGS. 2A-2N illustrate the formation of a CMUT structure that has a single CMUT cell. FIGS. 2A-2N also illustrate the formation of a bond pad structure. Further, silicon wafer 210 has a top surface which, in turn, has a CMUT surface region 211. In addition, silicon wafer 210 is heavily doped to have a resistance of 0.01 Ω/cm or less.

Method 200 begins by forming a patterned photoresist layer on the top surface of silicon wafer 210 in a conventional manner. After the patterned photoresist layer has been formed, the top surface of silicon wafer 210 is etched for a predefined time to form two or more front side alignment marks.

If a wet etchant is used, the resulting structure is rinsed following the etch. After the rinse, the patterned photoresist layer is conventionally removed, such as with an ash plus a solvent clean. Following the removal of the patterned photoresist layer, the resulting structure is cleaned to remove organics, such as with a Piranha etch (e.g., using a solution of 50 $H_2SO_4$: 1 $H_2O_2$ @ 120° C. removes approximately 240 nm/minute).

Next, as shown in FIG. 2A, method 200 continues by forming a post oxide structure 212 approximately 8500 Å thick on the top surface of silicon wafer 210 using the well-known local oxidation of silicon (LOCOS) process (e.g., the formation of a patterned hard mask followed by 1050° C. steam for 140 minutes). Post oxide structure 212 has a cell opening 213 (where the hard mask was placed and where a CMUT cell will be formed) approximately 60 µm wide that exposes and horizontally surrounds CMUT surface region 211. The LOCOS process also forms a backside oxide structure 214 that touches the bottom surface of silicon wafer 210 at the same time.

Following this, as shown in FIG. 2B, a cell oxide layer 216 approximately 4550 Å thick is grown in cell opening 212A on CMUT surface region 211 on the top surface of silicon wafer 210. The growth of cell oxide layer 216 causes post oxide structure 212 to continue growing, reaching a thickness of approximately 10500 Å.

After cell oxide layer 216 has been formed, as shown in FIG. 2C, a silicon-on-oxide (SOI) wafer 220 is fusion bonded to the top surface of post oxide structure 212 in a vacuum to form a vacuum-sealed cavity 222. Cavity 222, in turn, has a depth, which is measured vertically from the top surface of cell oxide layer 216 to the top surface of post oxide structure 212, of approximately 3100 Å.

SOI wafer 220 has a handle wafer 224, a buried insulation layer 226 approximately 1.1 µm thick that touches handle wafer 224, and a single-crystal silicon substrate structure 228 approximately 2.2 µm thick. Substrate structure 228, in turn, has a first surface that touches buried insulation layer 226, and a second surface that touches post oxide structure 212.

After substrate structure 228 has been fusion bonded to post oxide structure 212, as shown in FIG. 2D, handle wafer 224 is removed in a conventional manner, followed by the conventional removal of insulation layer 226. Next, as shown in FIG. 2E, a patterned photoresist layer 230 is formed on the first surface of substrate structure 228.

Once patterned photoresist layer 230 has been formed, as shown in FIG. 2F, the exposed region of substrate structure 228 is etched to form a CMUT membrane 232. The etch also re-exposes the alignment marks. (Alignment marks can alternately or additionally be formed on the backside of silicon wafer 210.) Patterned photoresist layer 230 is then removed in a conventional manner.

As shown in FIG. 2G, after the removal of patterned photoresist layer 230, a patterned photoresist layer 240 is formed on post oxide structure 212 and CMUT membrane 232. Once patterned photoresist layer 240 has been formed, as shown in FIG. 2H, the exposed region of post oxide structure 212 is etched until silicon wafer 210 has been exposed. The etch forms a substrate contact opening 241 that is approximately 50 µm wide. Patterned photoresist layer 240 is then removed in a conventional manner.

Following the removal of patterned photoresist layer 240, as shown in FIG. 2I, an aluminum layer 242 (which can optionally include copper) approximately 1500 Å thick is deposited to touch silicon wafer 210, post oxide structure 212, and CMUT membrane 232. After this, a patterned photoresist layer 250 is formed on aluminum layer 242.

Next, as shown in FIG. 2J, the exposed region of aluminum layer 242 is etched to form an aluminum bond pad 252 that extends through post oxide structure 212 to touch silicon wafer 210, and an aluminum plate 254 that touches and covers the top surface of CMUT membrane 232. Patterned photoresist layer 250 is then removed in a conventional manner.

As shown in FIG. 2K, after patterned photoresist layer 250 has been removed, a passivation layer 256 approximately 2000 Å thick is formed to touch and lie over post oxide structure 212, aluminum bond pad 252, and aluminum plate 254. Passivation layer 256 protects aluminum plate 254 from being damaged during subsequent packaging steps. CMUT membrane 232 and the portions of aluminum plate 254 and passivation layer 256 that lie over vacuum-sealed cavity 222 form a membrane stack 258. Once passivation layer 256 has been formed, a patterned photoresist layer 260 is formed on passivation layer 256.

After this, as shown in FIG. 2L, the exposed regions of passivation layer 256 are etched to form a bond pad opening 261 that exposes aluminum bond pad 252, and a bond pad opening, like a bond pad opening 138 in FIG. 1A, that exposes a bond pad region of aluminum plate 254. As shown in FIG. 2M, patterned photoresist layer 260 is then removed in a conventional manner.

Next, the resulting structure is flipped over for processing, and backside oxide structure 214 is removed in a conventional manner. For example, backside oxide structure 214 can be removed using chemical mechanical polishing. Alternately, backside oxide structure 214 can be removed using a single-sided wet etch, such as a SEZ etch by SEZ Austria GmbH, Draubodenweg 29, A-9500 Villach, Austria.

Following the removal of backside oxide structure 214, an acoustic damping structure 262, such as a tungsten epoxy mixture, is deposited onto the bottom side of silicon wafer 210 to form, as shown in FIG. 2N, a CMUT structure 264 with a CMUT cell 270. Silicon wafer 210 is then diced to form a number of individual die that each has one or more CMUT elements and cells.

Each CMUT cell 270 is designed to have a fractional bandwidth (FB) greater than 100% and a Q that is less than one. In addition, CMUT membrane 232 and the overlying portions of aluminum plate 254 and passivation layer 256 (membrane stack 258) are configured to vibrate at a maximum frequency of approximately 20 MHz.

One limitation of CMUT cell 270 is the ability to operate at higher frequencies (F0~40 MHz) while maintaining a fractional bandwidth greater than 100% and a Q less than one. A maximum frequency of 20 MHz is suitable for some contact or near contact body imaging applications, like echo cardiograms, but higher frequency operation would enable higher resolution medical imaging applications and non-destructive evaluation applications, such as the imaging of structural defects or the detection of frequency shifts due to chemical absorption. These applications require a maximum frequency of 40 MHz or more.

In order to operate at higher frequencies (>20 MHz) while maintaining the desired fractional bandwidth (>100%) and Q (<1), the thickness of membrane stack 258 must be reduced. Reducing the thickness of membrane stack 258 changes the frequency which, in turn, requires that the lateral dimension of vacuum-sealed cavity 222 be reduced accordingly.

To reduce the thickness of membrane stack 258, the thickness of silicon substrate structure 228, which becomes CMUT membrane 232, can be reduced. For example, the thickness of silicon substrate structure 228 can be reduced from 2.2 µm to 1 µm while maintaining structural stability. However, even a thickness of 1 µm is too large for efficient high frequency operation.

Additionally, the thickness of aluminum plate 254 can also be reduced to reduce the thickness of membrane stack 258. However, reducing the thickness of aluminum plate 254 is undesirable because the sheet resistance of aluminum plate 254 increases as the thickness of aluminum plate 254 is reduced.

For example, a 250 Å thick aluminum plate has a sheet resistance of approximately 1 Ω/square as compared to the approximate 180 mΩ/square sheet resistance of a 1500 Å thick aluminum plate. In a CMUT array, where the bond pad region lies a substantial distance away from the CMUT cells, it is undesirable for charge carriers to move this long a distance through a material that has a sheet resistance of 1 Ω/square.

With respect to passivation layer 256, the thickness of passivation layer 256 cannot be meaningfully reduced to reduce the thickness of membrane stack 258. This is because passivation layer 256 protects aluminum plate 254 during subsequent packaging steps. As a result, the thickness of passivation layer 256 is determined by the level of protection that is required, and may need to be increased if the thickness of aluminum plate 254 is reduced.

Thus, once the thickness of CMUT membrane 232 has been reduced as much as possible, there is still a need for an approach to further increase the maximum vibrational frequency of membrane stack 258.

BRIEF DESCRIPTION OF THE DRAWINGS

FIG. 1A is a plan view of CMUT array 100. FIG. 1B is a cross-sectional view of CMUT array 100 taken along line 1B-1B of FIG. 1A. FIG. 1C is a cross-sectional view of CMUT array 100 taken along line 1C-1C of FIG. 1A.

FIGS. 3A-3C are views illustrating an example of a CMUT array 300 in accordance with the present invention. FIG. 3A is a plan view of CMUT array 300. FIG. 3B is a cross-sectional view of CMUT array 300 taken along line 3B-3B of FIG. 3A. FIG. 3C is a cross-sectional view of CMUT array 300 taken along line 3C-3C of FIG. 3A.

FIG. 5A is a plan view of CMUT array 500. FIG. 5B is a cross-sectional view of CMUT array 500 taken along line 5B-5B of FIG. 5A. FIG. 5C is a cross-sectional view of CMUT array 500 taken along line 5C-5C of FIG. 5A.

FIG. 7A is a plan view of CMUT array 700. FIG. 7B is a cross-sectional view of CMUT array 700 taken along line 7B-7B of FIG. 7A. FIG. 7C is a cross-sectional view of CMUT array 700 taken along line 7C-7C of FIG. 7A.

DETAILED DESCRIPTION OF THE INVENTION

Figure 3A:
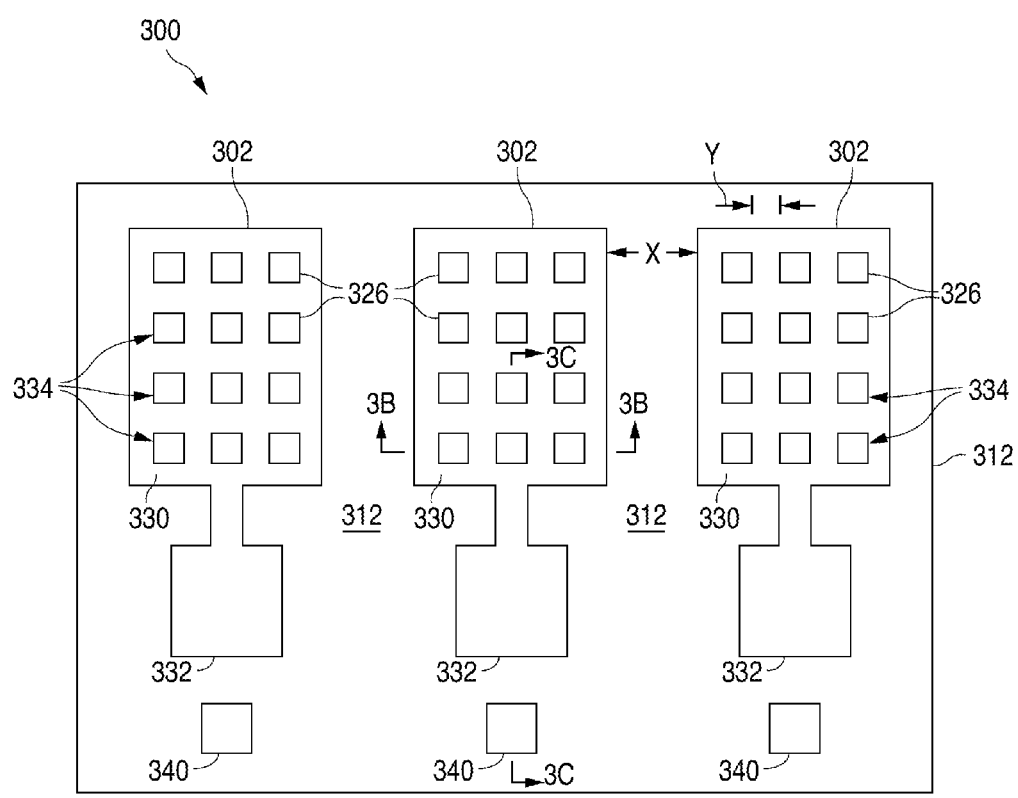

FIGS. 3A-3C show views that illustrate an example of a CMUT array 300 in accordance with the present invention. FIG. 3A shows a plan view of CMUT array 300, while FIG. 3B shows a cross-sectional view of CMUT array 300 taken along line 3B-3B of FIG. 3A, and FIG. 3C shows a cross-sectional view of CMUT array 300 taken along line 3C-3C of FIG. 3A.

As shown in the FIGS. 3A-3C example, CMUT array 300 has three CMUT elements 302 arranged in a single row, where each CMUT element 302 has 12 CMUT cells 304 arranged in an array three CMUT cells wide by four CMUT cells long. Further, each adjacent pair of CMUT elements 302 has a minimum spacing X of 16 μm, while each adjacent pair of CMUT cells 304 has a minimum spacing Y of 5 μm.

CMUT array 300 also includes a conventionally-formed semiconductor substrate 310, and a post structure 312 that touches semiconductor substrate 310. Semiconductor substrate 310 has a top surface which, in turn, has a number of spaced-apart CMUT surface regions 313. Further, in the present example, semiconductor substrate 310 is heavily doped to have a resistance of approximately 0.01 Ω/cm or less.

Post structure 312, which is non-conductive, horizontally surrounds, but does not cover, each CMUT surface region 313. In addition, in the present example, post structure 312 has a number of substrate contact openings 314 that extend completely through post structure 312 to expose semiconductor substrate 310. Post structure 312 can be implemented with, for example, oxide.

As additionally shown in FIGS. 3A-3C, CMUT array 300 includes a number of non-conductive structures 316, a corresponding number of silicon membranes 320, and a corresponding number of vacuum-sealed cavities 322. The non-conductive structures 316 touch the CMUT surface regions 313 on the top surface of semiconductor substrate 310. The silicon membranes 320, which are conductive, touch the top surface of post structure 312 and lie over and spaced apart from the non-conductive structures 316. Further, the vacuum-sealed cavities 322, which are horizontally surrounded by post structure 312, lie vertically between the non-conductive structures 316 and the silicon membranes 320.

In the present example, each of the silicon membranes 320 is approximately 1.0 μm thick. In addition, each cavity 322 has a depth, which is measured vertically from the top surface of non-conductive structure 316 to the top surface of post structure 312, of approximately 1200 Å.

CMUT array 300 further includes a number of metal silicide plates 326 that correspond with and cover the exposed surfaces of the silicon membranes 320. The metal silicide plates 326, which are spaced apart from each other, reduce the sheet resistances of the silicon membranes 320. Each metal silicide plate 326 has a top surface which, in turn, has a central region and a surrounding peripheral region. CMUT array 300 also includes a number of metal silicide pads 328 that lie in the substrate contact openings 314 to touch semiconductor substrate 310.

In addition, CMUT array 300 includes a number of aluminum structures 330 (which can optionally include copper). Each aluminum structure 330 touches post structure 312 and a group of metal silicide plates 326, where an aluminum structure 330 and a group of metal silicide plates 326 are part of a CMUT element 302.

Each aluminum structure 330 has a bond pad region 332, and a number of openings 334 that extend completely through aluminum structure 330 to expose the central regions of the metal silicide plates 326 within the group of metal silicide plates. As a result, each aluminum structure 330 touches the peripheral regions of the metal silicide plates 326 within the group of metal silicide plates. The aluminum structures 330 provide low-resistance paths from the metal silicide plates 326 to the bond pad regions 332 on the aluminum structures 330. A bond pad region 332 is a region where a wire will be subsequently bonded.

In the present example, each metal silicide plate 326 has a thickness of approximately 250 Å and a sheet resistance of approximately 4-5 Ω/square, while aluminum structure 330 has a thickness of approximately 8500 Å and a sheet resistance of approximately 32 mΩ/square. Thus, the sheet resistance from a bond pad region 332 to the points that lie over the centers of the vacuum-sealed cavities 322 is a combination of the sheet resistance of aluminum structure 330 and the sheet resistances of the metal silicide plates 326. As a result, aluminum structure 330 provides sheet resistance compensation to the metal silicide plates 326.

CMUT array 300 further includes a number of aluminum bond pads 340 (which can optionally include copper) that lie within the substrate contact openings 314 to make electrical connections to the metal silicide pads 328. In the present example, a metal silicide pad 328 has a thickness of approximately 250 Å, while aluminum bond pad 340 has a thickness of approximately 8500 Å.

The silicon membranes 320 and the overlying metal silicide plates form a number of membrane stacks 342 that lie directly over a corresponding number of vacuum-sealed cavities 322. The membrane stacks 342, along with the vacuum-sealed cavities 322 and the non-conductive structures 316, form the CMUT cells 304. Further, CMUT array 300 optionally has an acoustic dampening structure 344 that touches the bottom surface of semiconductor substrate 310.

In operation, a first bias voltage is placed on semiconductor substrate 310, which functions as a first capacitor plate, and a second bias voltage is placed on the silicon membranes 320, which function as second capacitor plates. Thus, the voltages across the capacitor plates lie across the vacuum-sealed cavities 322.

When used as a receiver, an ultrasonic wave causes the membrane stacks 342 to vibrate. The vibration varies the capacitance across the first and second capacitor plates, thereby generating an electrical signal that varies as the capacitance varies. When used as a transmitter, an alternating electrical signal applied across the biased first and second capacitor plates causes the membrane stacks 342 to vibrate which, in turn, transmits ultrasonic waves.

In addition to transmitting ultrasonic waves outward, ultrasonic waves are also transmitted backward towards the bottom surface of semiconductor substrate 310. These backward ultrasonic waves can resonate within semiconductor substrate 310 depending on the thickness of semiconductor substrate 310 and the frequency of operation, and can interfere with the quality of the resultant image. When present, acoustic dampening structure 344 absorbs and dampens the ultrasonic waves in semiconductor substrate 310.

One of the advantages of the present example is that CMUT array 300 replaces a thick aluminum plate with a much thinner metal silicide plate. Another advantage of the present invention is that CMUT array 300 eliminates the need for the thick passivation layer which, in turn, eliminates the need for a costly masking step. The thick passivation layer can be eliminated because the metal silicide plates 326 and aluminum structures 330 do not require protection during sequent packaging steps.

As a result, once the thicknesses of the CMUT membranes 320 have been reduced as much as possible, the total thickness of the material overlying a CMUT membrane 320 in the present invention is substantially less than the total thicknesses of aluminum plate 126 and passivation layer 132 in prior-art CMUT array 100.

For example, by eliminating the 2000 Å thick passivation layer 132, and by replacing the 1500 Å thick aluminum plate 126 of prior-art array 100 with a metal silicide plate 326 that is 250 Å thick, the thickness of the material overlying a CMUT membrane 320 is reduced by approximately 3250 Å. By reducing the thickness of the material that lies over CMUT membrane 320, along with reducing the thickness of CMUT membrane 320, the maximum rate of vibration can be increased by reducing the lateral dimension of vacuum-sealed cavity 322. Thus, vibration rates of 40 MHz or more can be reached while maintaining a fractional bandwidth greater than 100% and a Q less than one.

Figure 1A:
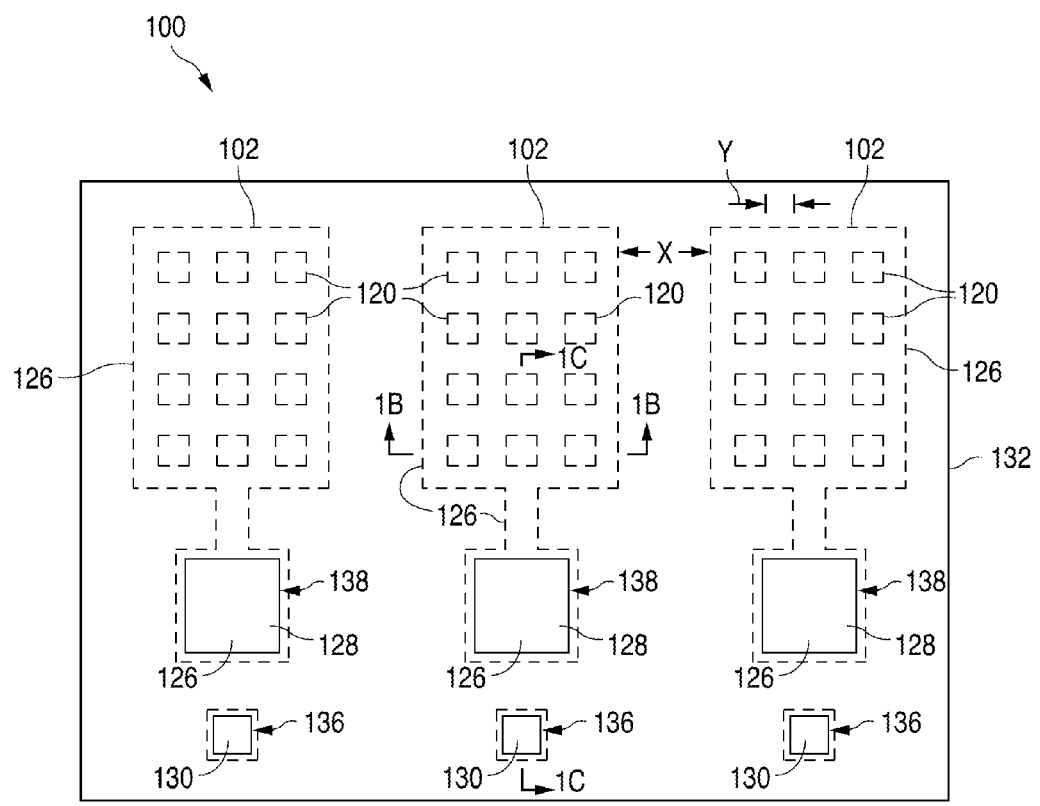
FIGS. 1A-1C are views illustrating a prior-art CMUT array 100.
Figure 1B:
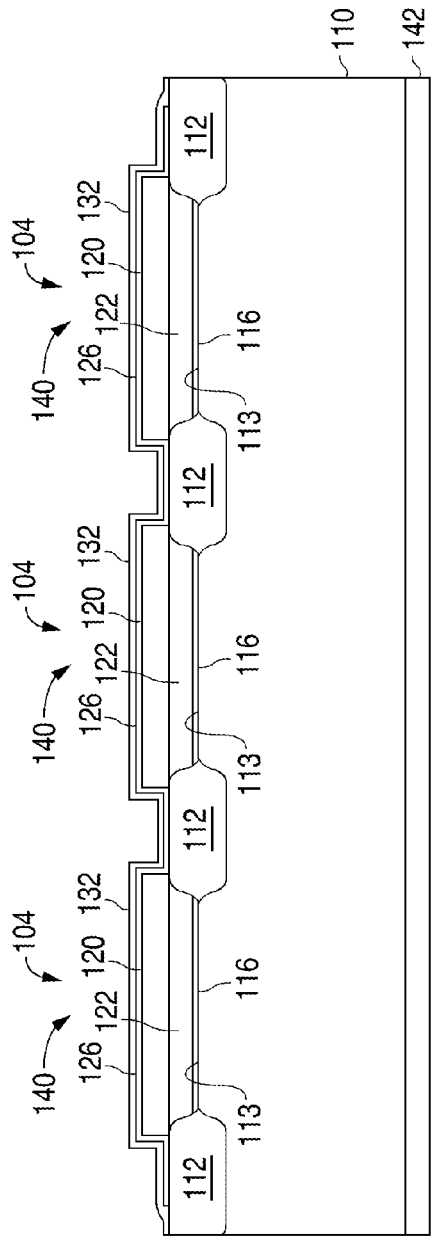
Figure 1C:
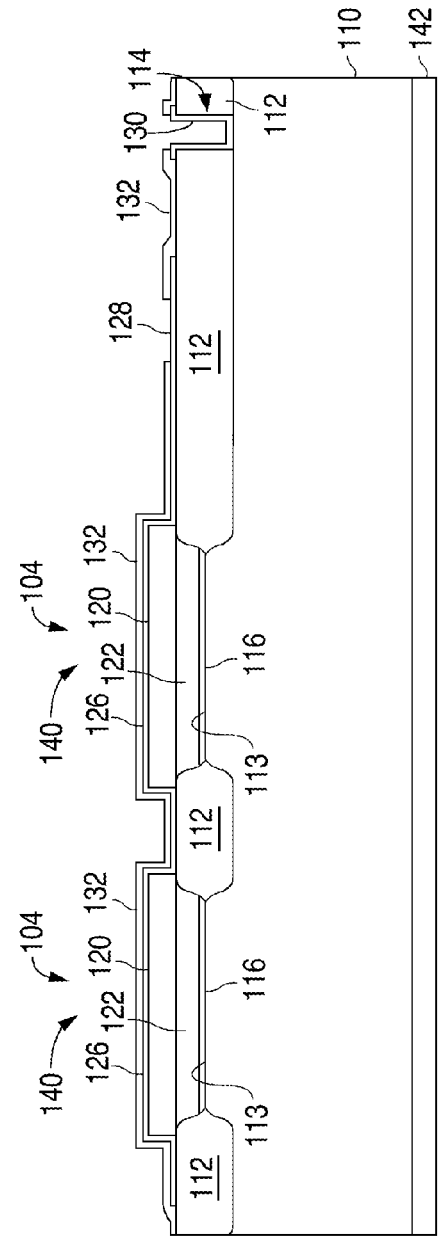
Figure 2A:
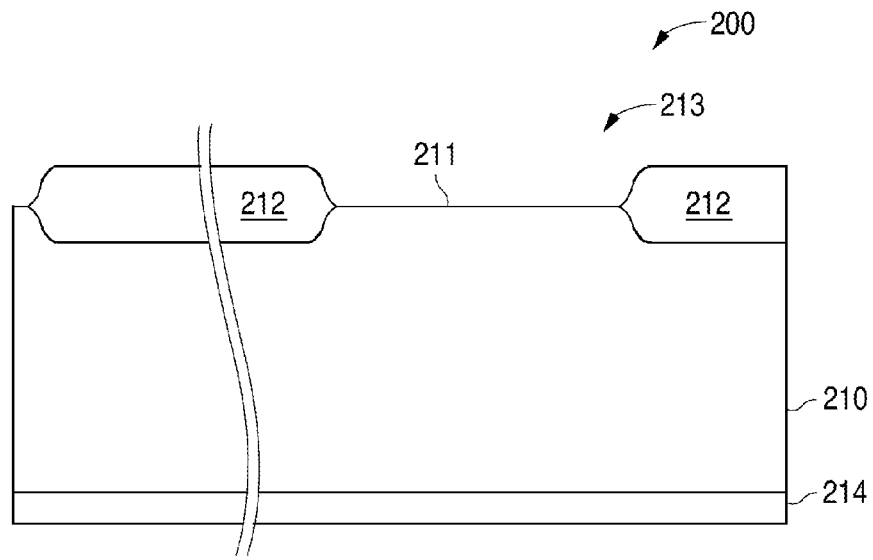
FIGS. 2A-2N are cross-sectional views illustrating a prior-art method 200 of forming a CMUT structure.
Figure 2B:
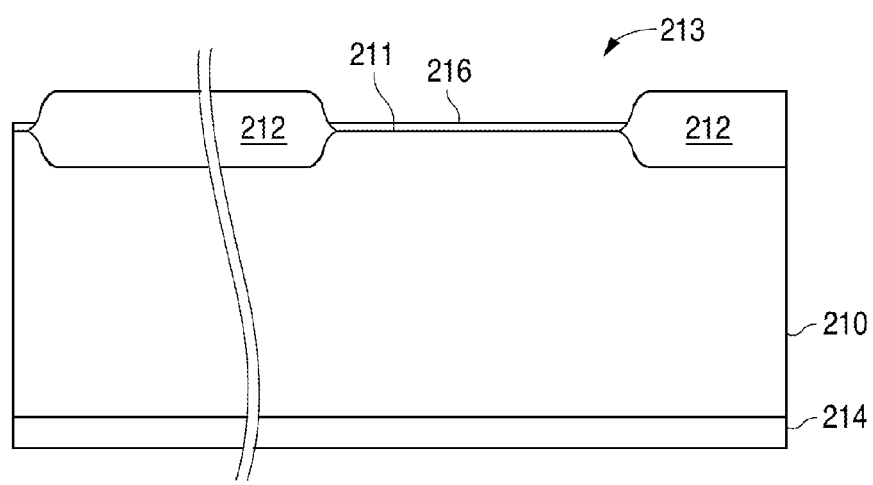
Figure 2C:
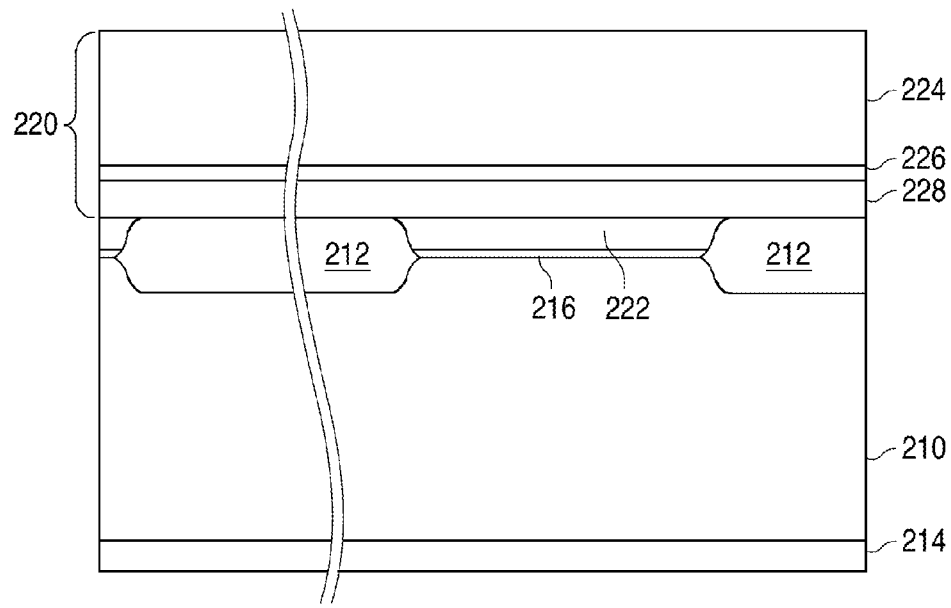
Figure 2D:
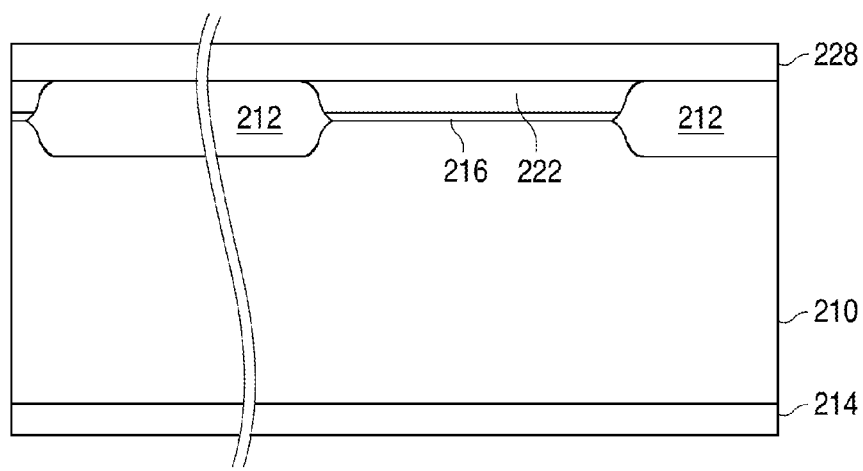
Figure 2E:
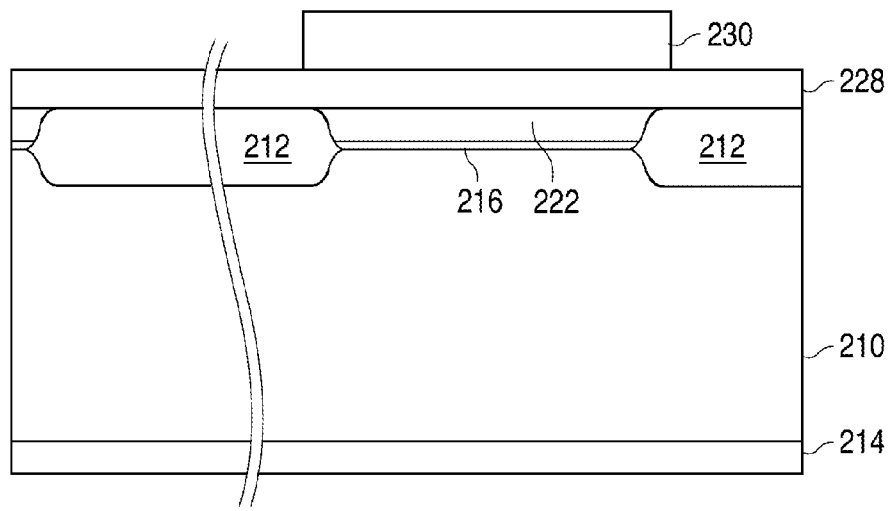
Figure 2F:
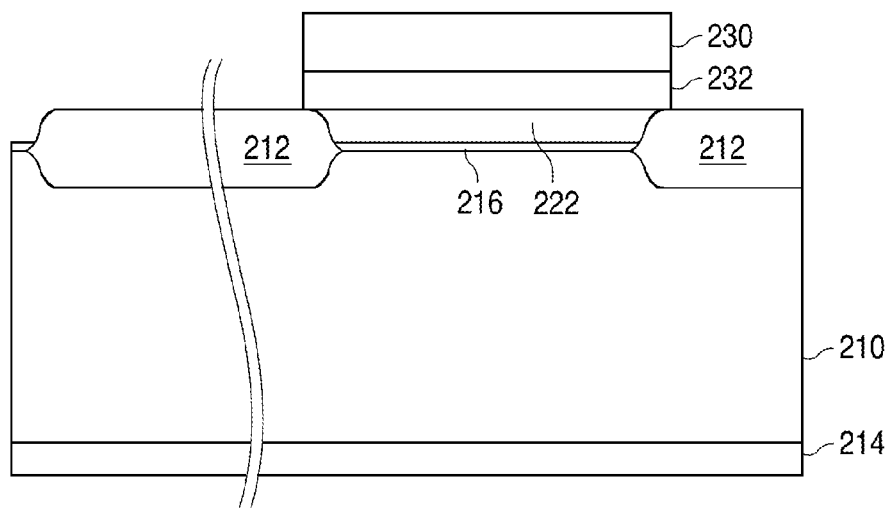
Figure 2G:
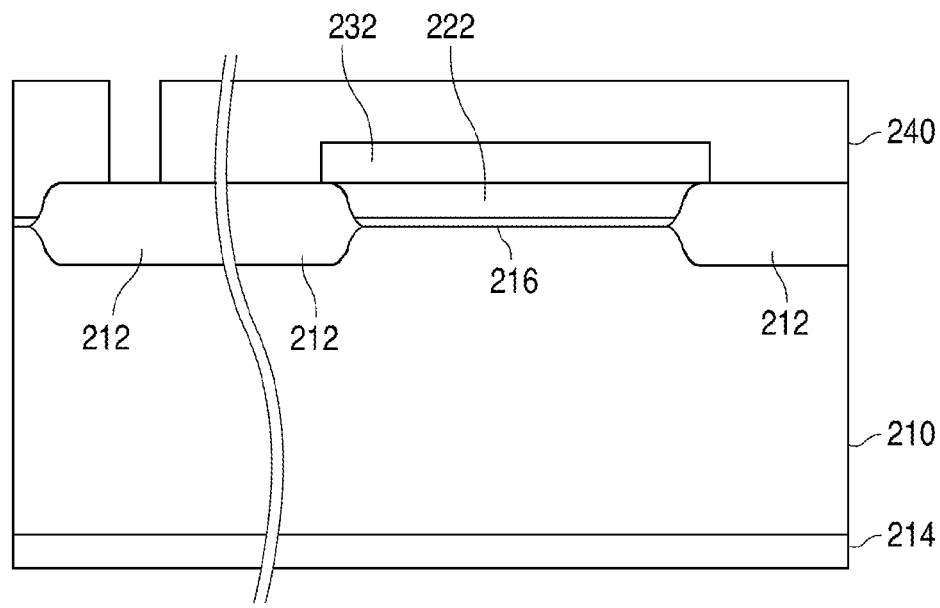
Figure 2H:
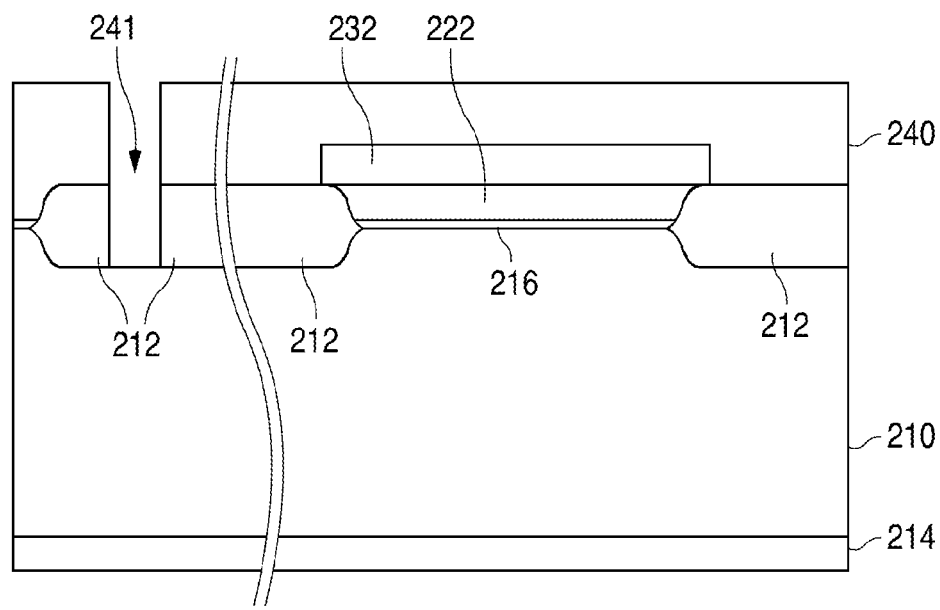
Figure 2I:
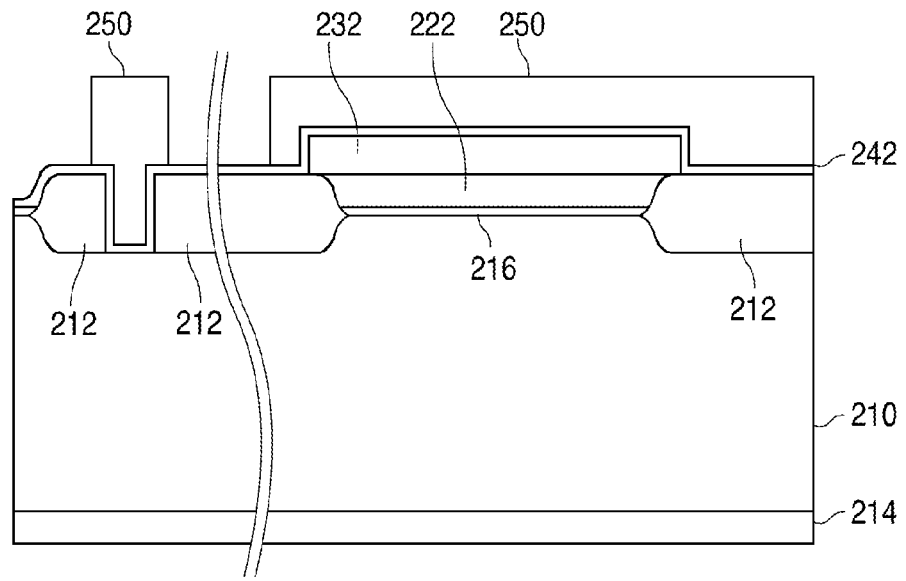
Figure 2J:
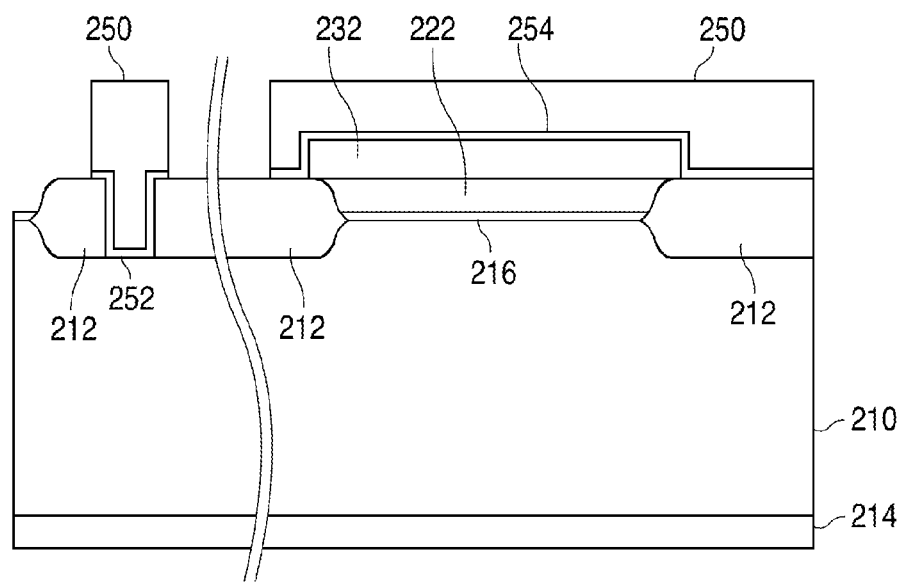
Figure 2K:
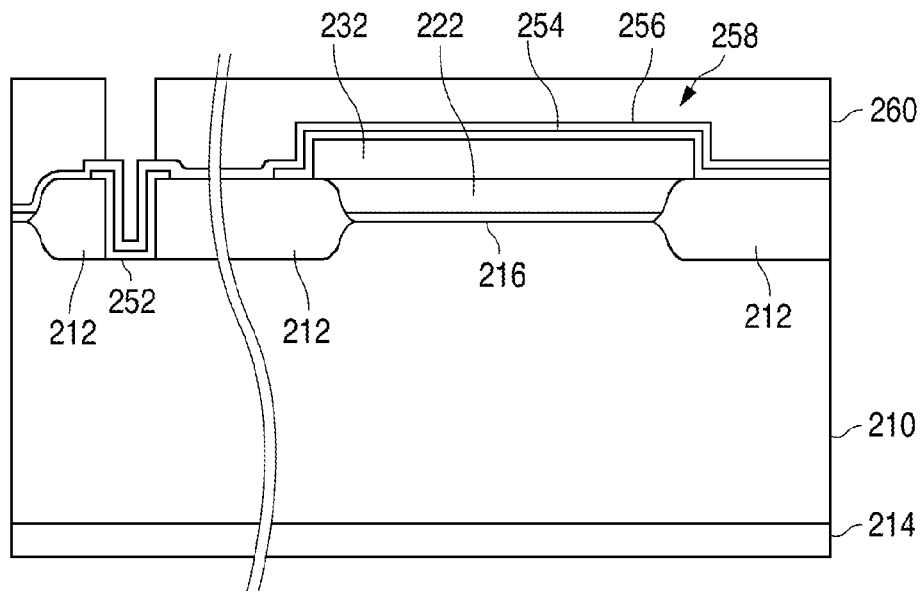
Figure 2L:
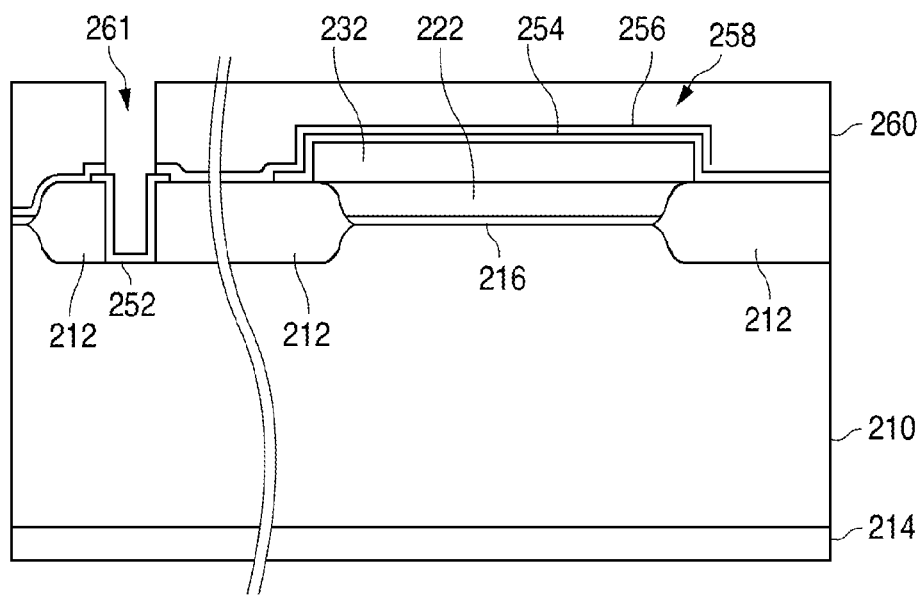
Figure 2M:
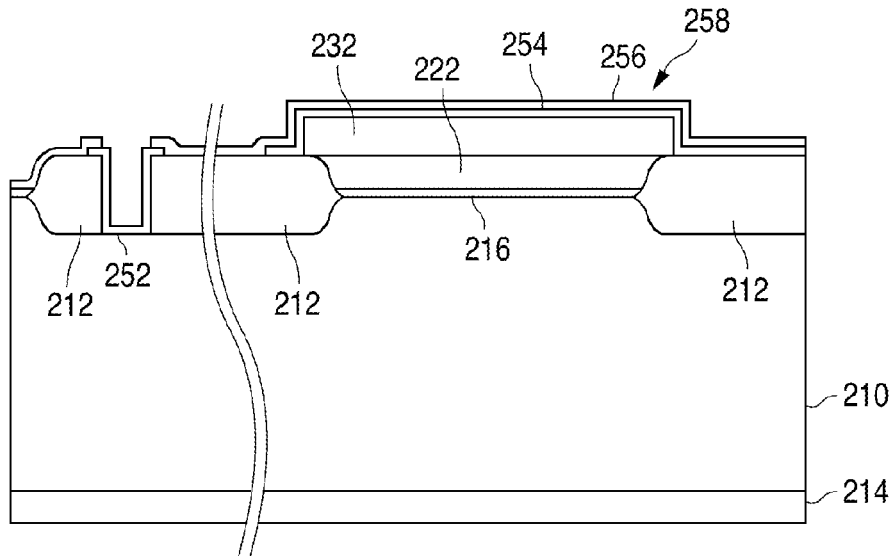
Figure 2N:
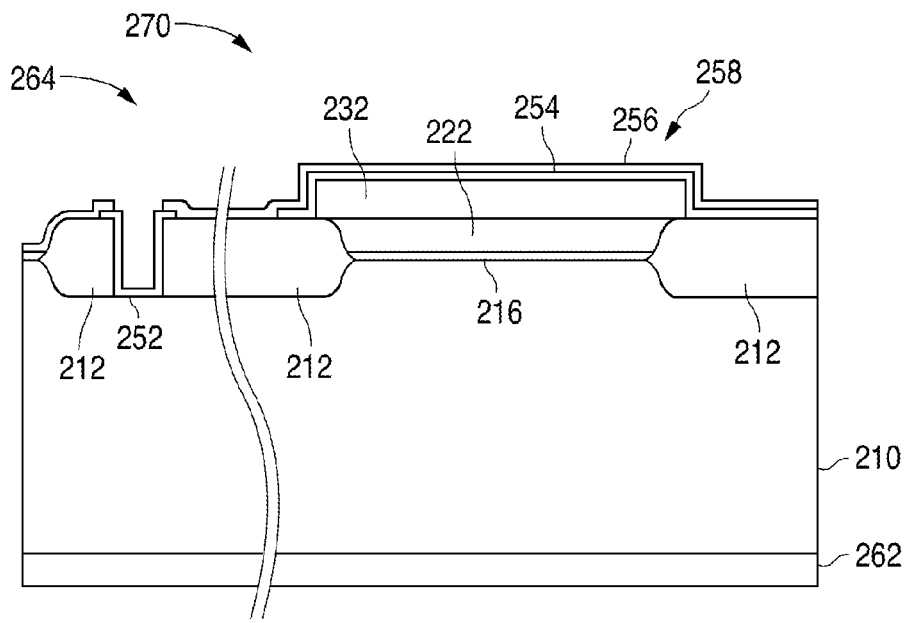

FIGS. 4A-4D show cross-sectional views that illustrate an example of a method 400 of forming a CMUT structure in accordance with the present invention. Method 400 is the same as prior-art method 200 up through the removal of patterned photoresist layer 240 shown in FIG. 2H, except that in method 400 post oxide structure 212 and cell oxide layer 216 are thinner.

In addition, in method 400, cavity 222, which is measured vertically from the top surface of cell oxide layer 216 to the top surface of post oxide structure 212, has a depth of approximately 1200 Å. As a result, method 400 utilizes the same reference numerals as method 200 to designate the structures which are common to both methods.

Figure 4A:
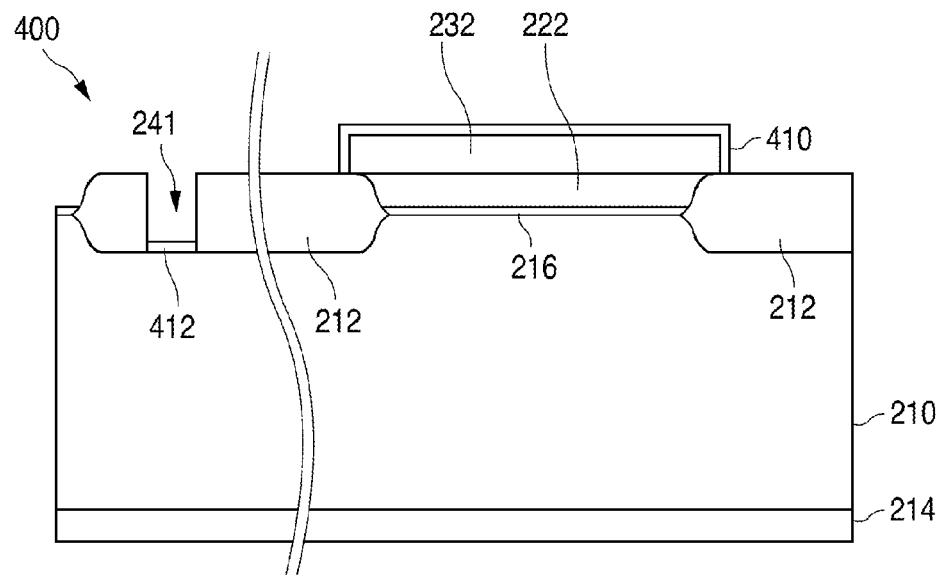
FIGS. 4A-4D are cross-sectional views illustrating an example of a method 400 of forming a CMUT structure in accordance with the present invention.

As shown in FIG. 4A, after patterned photoresist layer 240 has been removed, method 400 continues with conventional metal silicide steps to form a metal silicide plate 410 on CMUT membrane 232, and a metal silicide pad 412 in substrate contact opening 241 on the exposed region of semiconductor substrate 210. Metal silicide plate 410, in turn, has a top surface with a central region and a surrounding peripheral region.

For example, a silicide material such as cobalt, platinum, titanium, or nickel can be sputter deposited to a depth of approximately 250 Å. Alternately, 200 Å of cobalt followed by 50 Å of titanium, which forms a cap that prevents silicide crawl out, can also be used. After the silicide material has been sputter deposited, an initial rapid thermal process is conventionally performed, such as 525° C. for one minute in $N_2$.

Following the initial rapid thermal process, the unreacted silicide material is wet stripped from post oxide structure 212 using, for example, $H_3PO_4/H_2O_2$ for 20 minutes. Once the unreacted material has been stripped, a second rapid thermal process is performed, such as at 800° C. for one minute in $N_2$. The second rapid thermal process completes the silicide reaction.

Figure 4B:
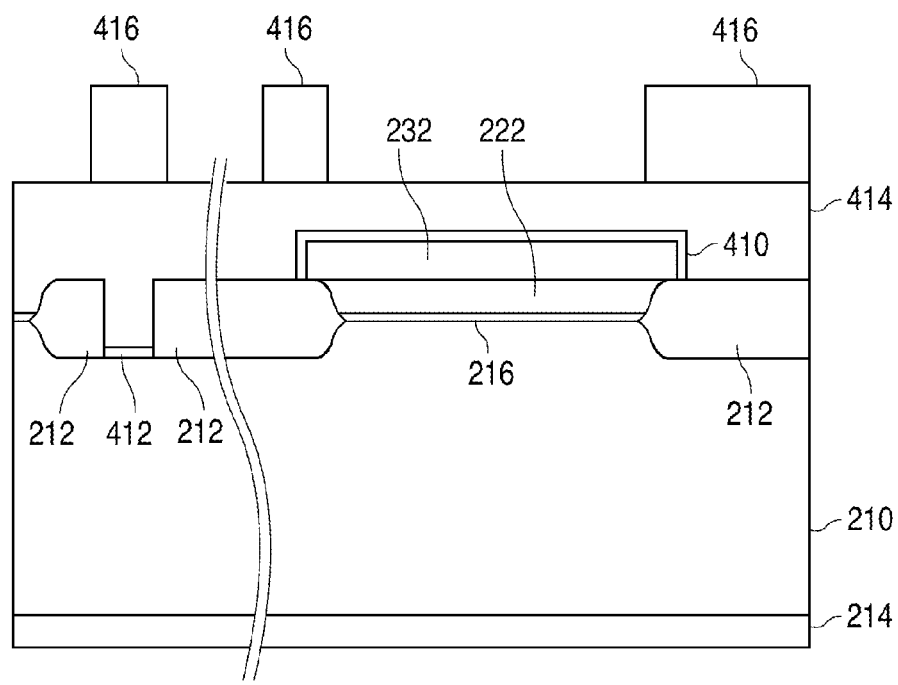

As shown in FIG. 4B, following the formation of metal silicide plate 410 and metal silicide pad 412, an aluminum layer 414 (which can optionally include copper) approximately 8500 Å thick is deposited to touch post oxide structure 212, metal silicide plate 410, and metal silicide pad 412. After this, a patterned photoresist layer 416 is formed on aluminum layer 414.

Figure 4C:
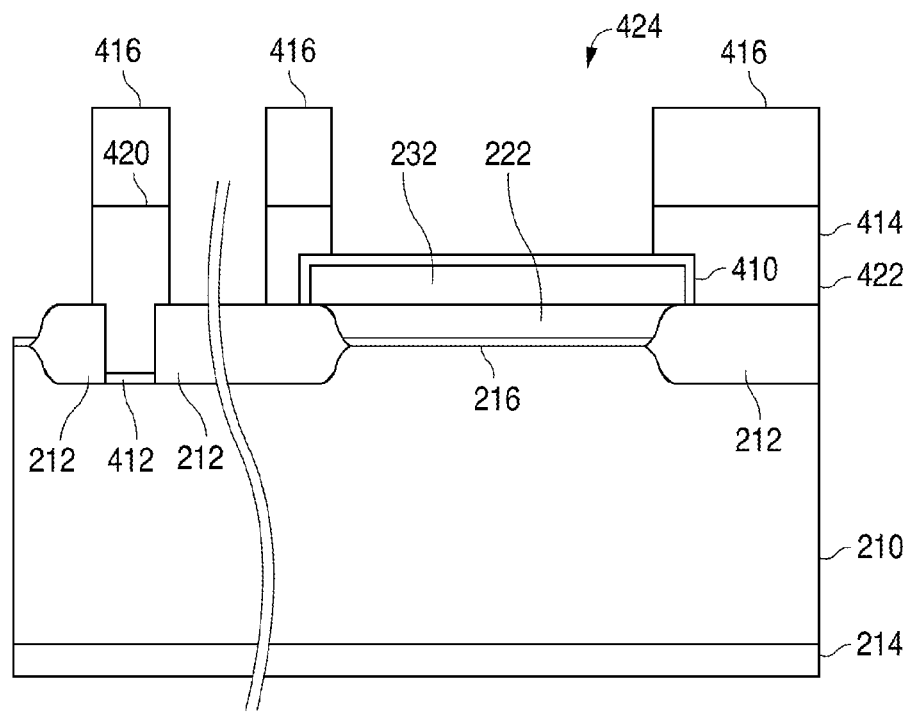

Next, as shown in FIG. 4C, the exposed regions of aluminum layer 414 are etched to form an aluminum bond pad 420 that lies above and extends through post oxide structure 212 to touch metal silicide pad 412, and an aluminum structure 422 that touches post oxide structure 212 and metal silicide plate 410. In addition, the etch forms an opening 424 in aluminum structure 422 that exposes the central region of metal silicide plate 410, leaving aluminum structure 422 touching the peripheral region of metal silicide plate 410. Patterned photoresist layer 416 is then removed in a conventional manner.

If an acoustic dampening structure is required, the resulting structure is next flipped over for processing, and backside oxide structure 214 is removed in a conventional manner. For example, backside oxide structure 214 can be removed using chemical mechanical polishing. Alternately, backside oxide structure 214 can be removed using a single-sided wet etch, such as a SEZ etch.

Figure 4D:
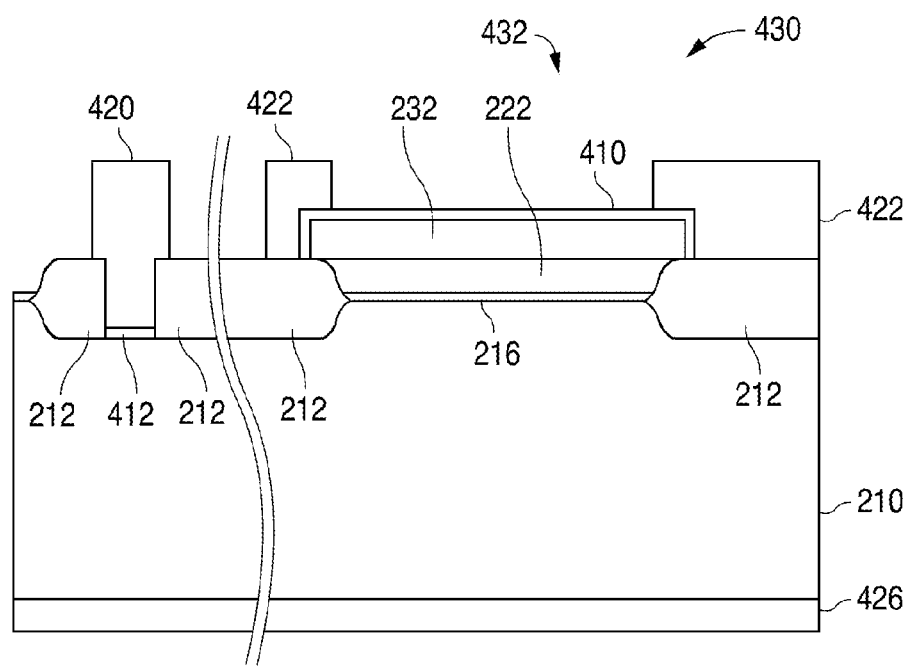

Following the removal of backside oxide structure 214, an acoustic damping structure 426, such as a tungsten epoxy mixture, is formed in a conventional manner on the bottom side of silicon wafer 210 to form, as shown in FIG. 4D, a CMUT structure 430 that has a CMUT cell 432. Silicon wafer 210 is then diced to form a number of individual die that each has one or more CMUT elements and cells.

Figure 5A:
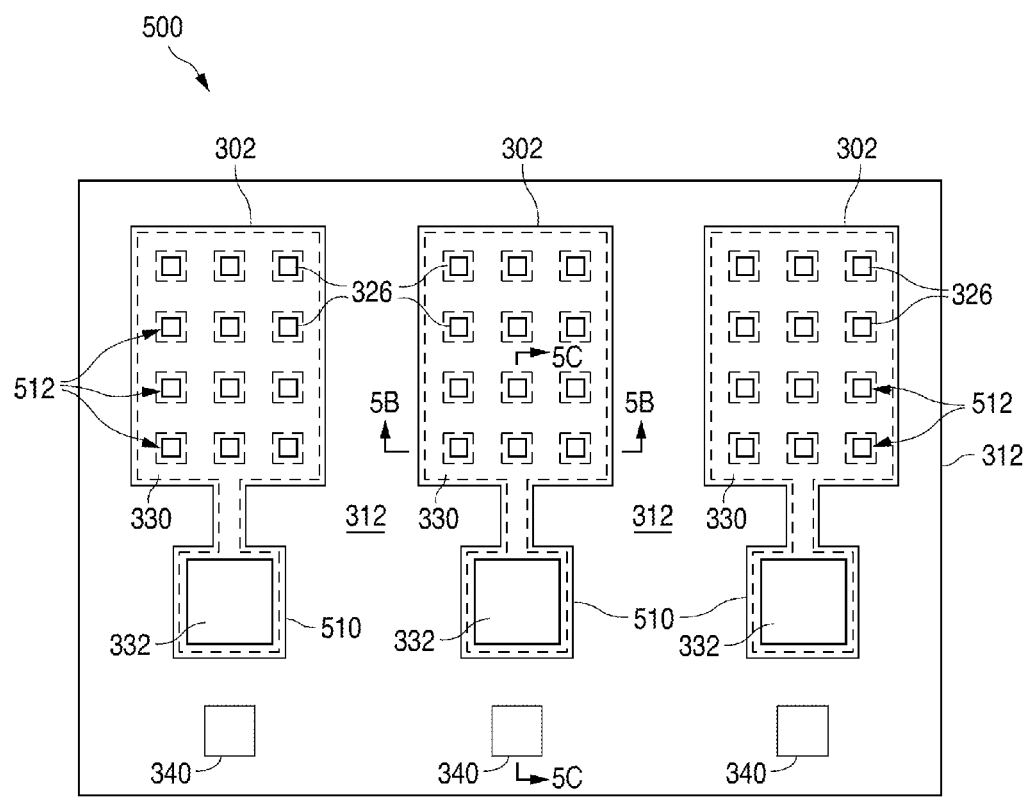
FIGS. 5A-5C are views illustrating an example of a CMUT array 500 in accordance with an alternate embodiment of the present invention.
Figure 5B:
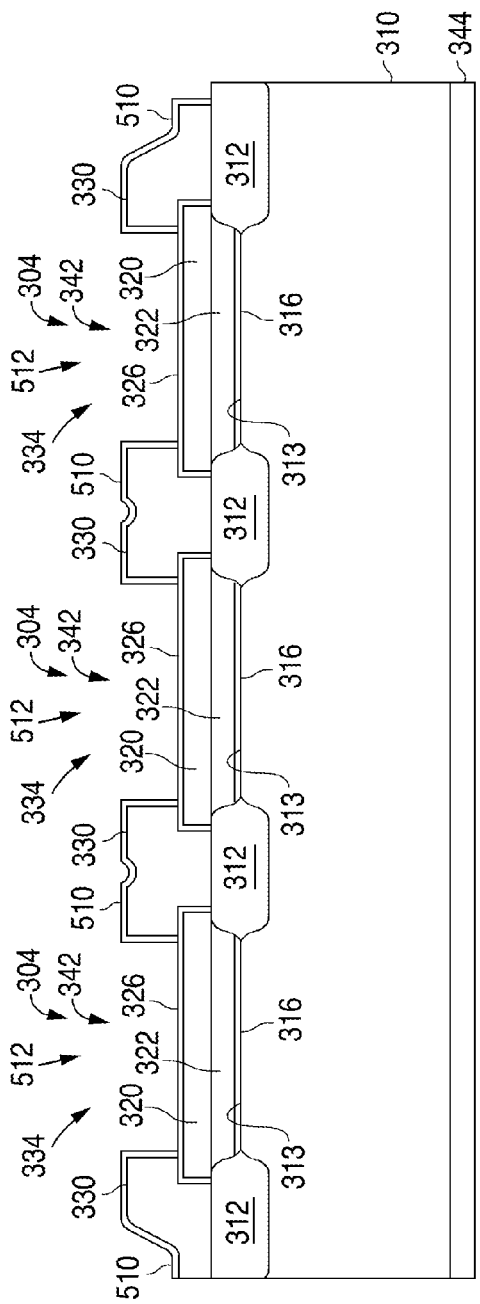
Figure 5C:
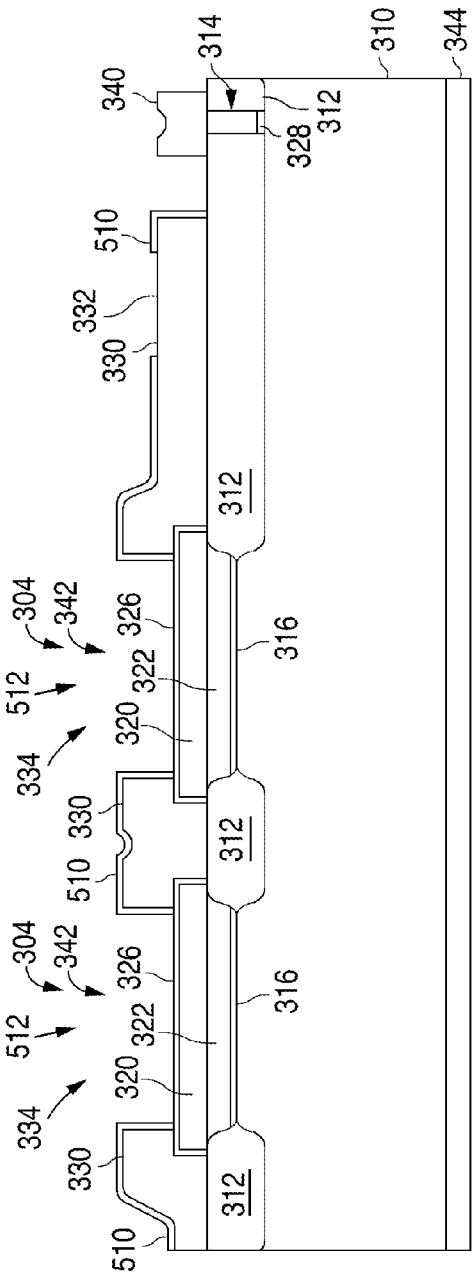

FIGS. 5A-5C show views that illustrate an example of a CMUT array 500 in accordance with an alternate embodiment of the present invention. FIG. 5A shows a plan view of CMUT array 500, while FIG. 5B shows a cross-sectional view of CMUT array 500 taken along line 5B-5B of FIG. 5A, and FIG. 5C shows a cross-sectional view of CMUT array 500 taken along line 5C-5C of FIG. 5A.

CMUT array 500 is similar to CMUT array 300 and, as a result, utilizes the same reference numerals to designate the structures which are common to both CMUT arrays. As shown in FIGS. 5A-5C, CMUT array 500 differs from CMUT array 300 in that CMUT array 500 includes a number of passivation structures 510 that touch and lie over the aluminum structures 330.

Each passivation structure 510, in turn, includes a number of openings 512 that expose the metal silicide plates 326 and the bond pad regions. Thus, a passivation layer can alternately be formed over the aluminum structures 330 to protect the aluminum structures 330 without also being formed to cover all of the metal silicide plates 326. As a result, no passivation layer lies over the central regions of the metal silicide plates 326.

Figure 6A:
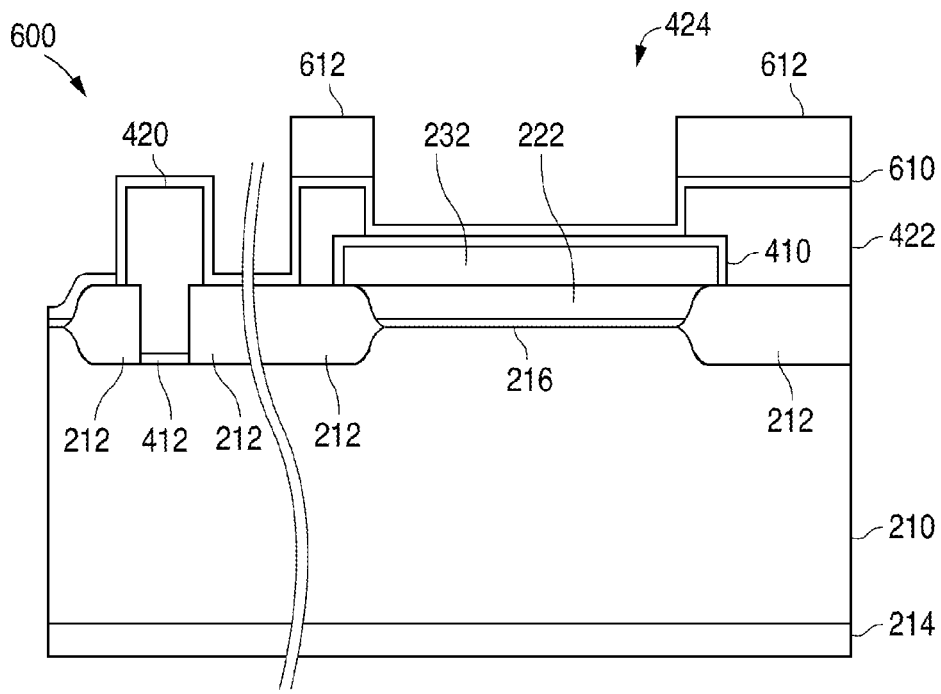
FIGS. 6A-6C are cross-sectional views illustrating an example of a method 600 of forming a CMUT structure in accordance with an alternate embodiment of the present invention.
Figure 6B:
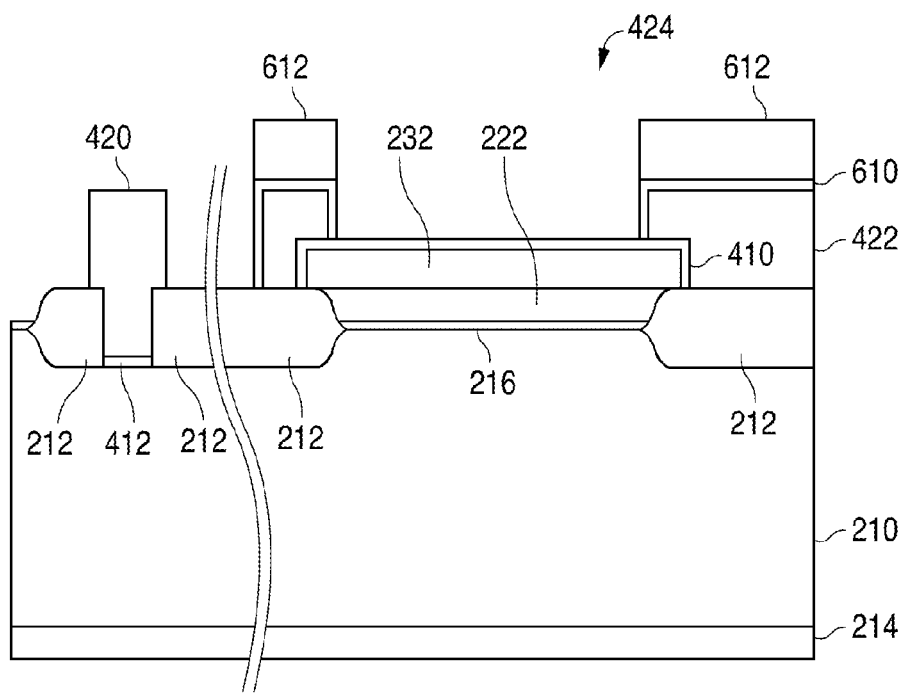
Figure 6C:
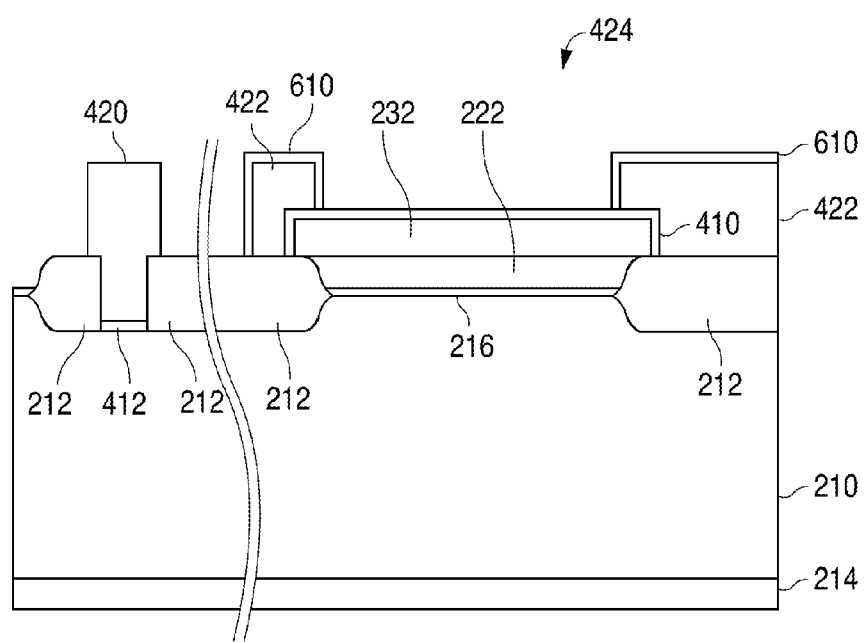

FIGS. 6A-6C show cross-sectional views that illustrate an example of a method 600 of forming a CMUT structure in accordance with an alternate embodiment of the present invention. Method 600 is the same as method 400 up through the removal of patterned photoresist layer 416 shown in FIG. 4C, and continues as shown in FIG. 6A with the deposition of a passivation layer 610 on metal silicide plate 410, aluminum bond pad 420, and aluminum structure 422. Once passivation layer 610 has been formed, a patterned photoresist layer 612 is formed on passivation layer 610 in a conventional manner.

After this, as shown in FIG. 6B, the exposed regions of passivation layer 610 are etched to expose aluminum bond pad 420, the central region of metal silicide plate 410, and the bond pad region of aluminum structure 422. As shown in FIG. 6C, patterned photoresist layer 612 is then removed in a conventional manner. If an acoustic dampening structure is required, the resulting structure is next flipped over and processing continues as in method 400 to form backside oxide structure 426.

Figure 7A:
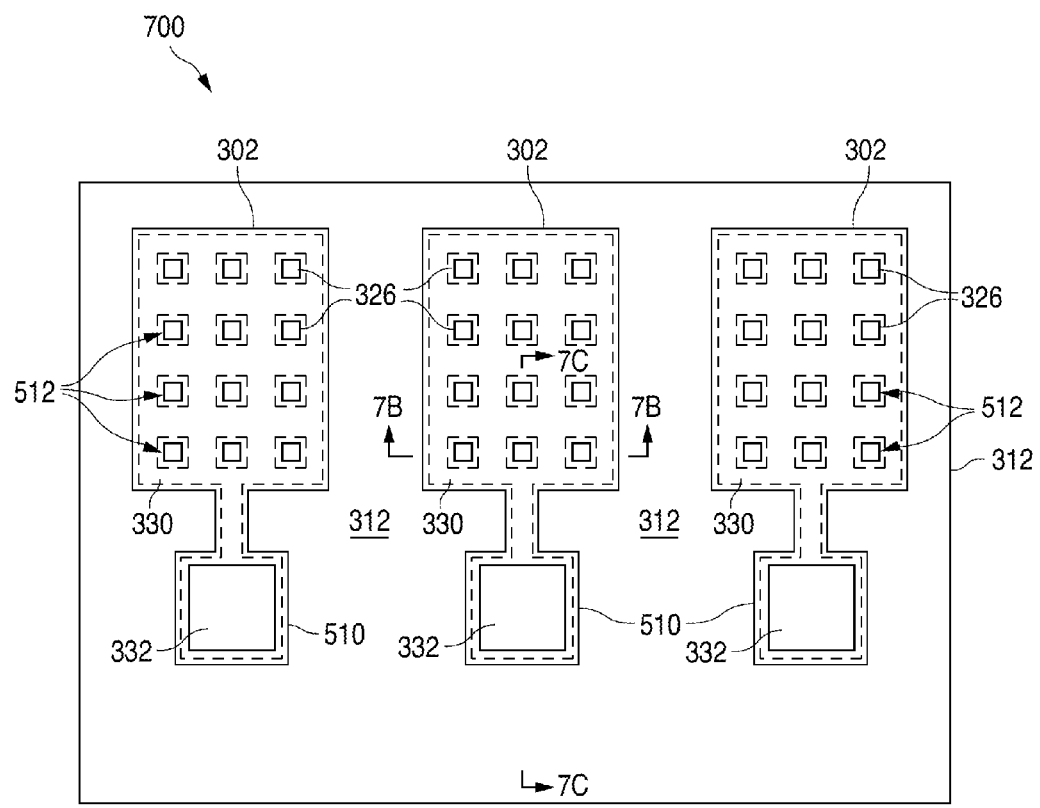
FIGS. 7A-7C are views illustrating an example of a CMUT array 700 in accordance with an alternate embodiment of the present invention.
Figure 7B:
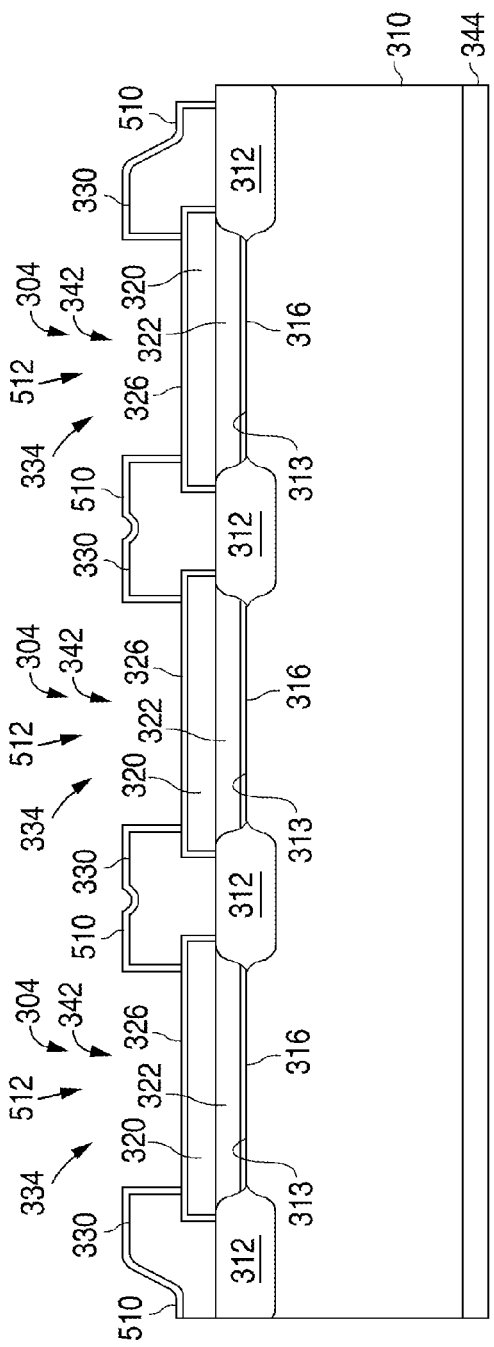
Figure 7C:
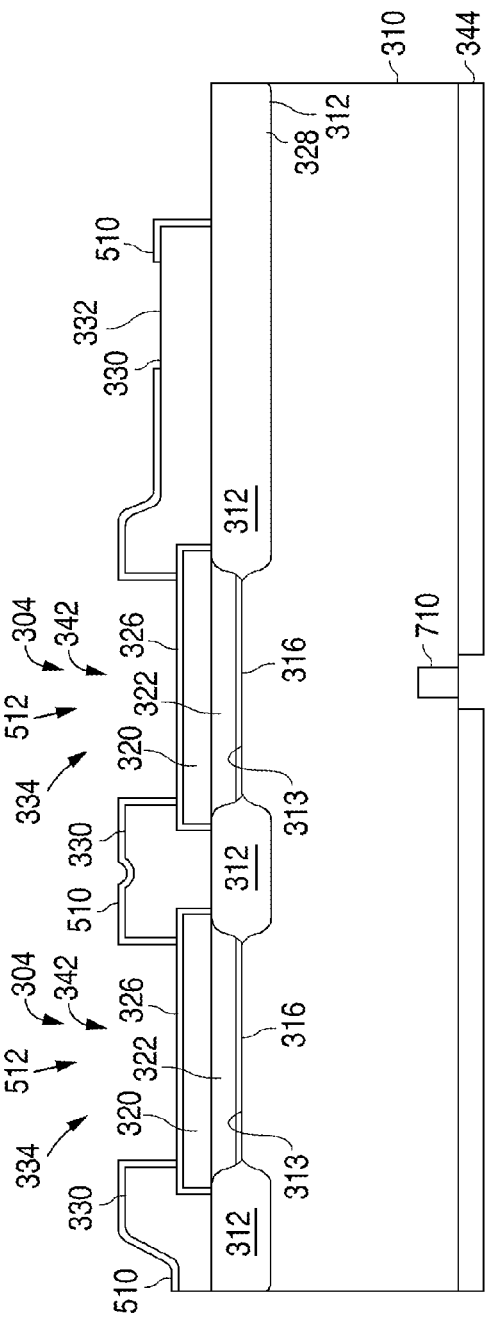

FIGS. 7A-7C show views that illustrate an example of a CMUT array 700 in accordance with an alternate embodiment of the present invention. FIG. 7A shows a plan view of CMUT array 700, while FIG. 7B shows a cross-sectional view of CMUT array 700 taken along line 7B-7B of FIG. 7A, and FIG. 7C shows a cross-sectional view of CMUT array 700 taken along line 7C-7C of FIG. 7A.

CMUT array 700 is similar to CMUT array 500 and, as a result, utilizes the same reference numerals to designate the structures which are common to both CMUT arrays. As shown in FIGS. 7A-7C, CMUT array 700 differs from CMUT array 500 in that CMUT array 700 includes a number of backside contacts 710 that extend into semiconductor substrate 310 to touch and make an electrical connection with semiconductor substrate 310.

Because semiconductor substrate 310 is heavily doped, the backside contacts 710 make ohmic contacts to semiconductor substrate 310. In addition, since the electrical connection to semiconductor substrate 310 is made from the backside, the substrate contact openings 314, the metal silicide pads 328, and the aluminum bond pads 340 can be omitted. Further, the passivation structure 510 can alternately be omitted such that CMUT array 300 is formed with backside contacts and without the substrate contact openings 314, the metal silicide pads 328, and the aluminum bond pads 340.

The backside contacts 710 can be formed after backside oxide structure 214 has been removed in the same manner that the backside aluminum plugs 390 are formed in U.S. Pat. No. 7,646,064 issued on Jan. 12, 2010 to Visvamohan Yegnashankaran, which is hereby incorporated by reference. Following the formation of the backside contacts 710, if an acoustic dampening structure is required, acoustic damping structure 426 is next formed as before, except that an opening is formed in acoustic damping structure 426 in a conventional manner to expose the backside contacts 710.

It should be understood that the above descriptions are examples of the present invention, and that various alternatives of the invention described herein may be employed in practicing the invention. Thus, it is intended that the following claims define the scope of the invention and that structures and methods within the scope of these claims and their equivalents be covered thereby.

What is claimed is:

1. A transducer structure comprising:
a substrate having a conductivity type and a surface region;
a post structure that touches the substrate, the post structure having a top surface and being non-conductive;
a first conductive structure that touches the top surface of the post structure, the first conductive structure having a top surface and lying over and spaced apart from the surface region of the substrate, the top surface of the first conductive structure having a central region and a surrounding peripheral region; and
a second conductive structure that touches the peripheral region of the first conductive structure, the second conductive structure having an opening that extends completely through the second conductive structure to expose the central region of the top surface of the first conductive structure;
wherein the second conductive structure touches the top surface of the post structure.

2. The transducer structure of claim 1 wherein the second conductive structure has a top surface, the top surface of the second conductive structure having a bond pad region.

3. The transducer structure of claim 1 wherein the first conductive structure includes a silicon membrane and a metal silicide plate that touches and overlies the silicon membrane.

4. The transducer structure of claim 1 and further comprising a non-conductive structure that touches the surface region of the substrate.

5. The transducer structure of claim 4 and further comprising a vacuum-sealed cavity that lies between and touches the silicon membrane and the non-conductive structure.

6. The transducer structure of claim 1 and further comprising:
a metal silicide pad that touches the substrate; and
a conductive bond pad that touches the metal silicide pad, the post structure touching and horizontally surrounding a portion of the conductive bond pad.

7. The transducer structure of claim 1 and further comprising a passivation structure that touches the second conductive structure, the passivation structure having an opening that exposes the central region of the first conductive structure.

8. The transducer structure of claim 1 and further comprising a conductive bond pad that touches a bottom surface of the substrate.

9. The transducer structure of claim 1 wherein the post structure laterally surrounds the surface region.

10. A method of forming a transducer structure comprising:
   forming a post structure that touches a substrate, the post structure having a top surface and being non-conductive, the substrate having a conductivity type and a surface region;
   forming a first conductive structure that touches the top surface of the post structure, the first conductive structure having a top surface and lying over and spaced apart from the surface region of the substrate, the top surface of the first conductive structure having a central region and a surrounding peripheral region; and
   forming a second conductive structure that touches the peripheral region of the first conductive structure, the second conductive structure having an opening that extends completely through the second conductive structure to expose the central region of the top surface of the first conductive structure;
   wherein the second conductive structure touches the top surface of the post structure.

11. The method of claim 10 wherein forming a first conductive structure includes:
   etching a substrate structure that touches the post structure to form a membrane; and
   siliciding the membrane to form the first conductive structure.

12. The method of claim 10 wherein the first conductive structure includes a silicon membrane and a metal silicide plate that touches and overlies the silicon membrane.

13. The method of claim 10 and further comprising forming a non-conductive structure that touches the surface region of the substrate.

14. The method of claim 13 wherein a vacuum-sealed cavity lies between and touches the silicon membrane and the non-conductive structure.

15. The method of claim 10 and further comprising:
   forming a metal silicide pad that touches the substrate; and
   forming a conductive bond pad that touches the metal silicide pad, the post structure touching and horizontally surrounding a portion of the conductive bond pad.

16. The method of claim 10 and further comprising forming a passivation structure that touches the second conductive structure, the passivation structure having an opening that exposes the central region of the first conductive structure.

17. The method of claim 10 and further comprising forming a conductive bond pad that touches a bottom surface of the substrate.

18. The method of claim 10 wherein the post structure laterally surrounds the surface region.

\* \* \* \* \*